(12) United States Patent
Hirayama

(10) Patent No.: US 12,318,070 B2
(45) Date of Patent: Jun. 3, 2025

(54) ENDOSCOPE

(71) Applicant: HOYA CORPORATION, Tokyo (JP)

(72) Inventor: Tetsu Hirayama, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 462 days.

(21) Appl. No.: 17/767,214

(22) PCT Filed: Sep. 30, 2020

(86) PCT No.: PCT/JP2020/037103
§ 371 (c)(1),
(2) Date: Apr. 7, 2022

(87) PCT Pub. No.: WO2021/075262
PCT Pub. Date: Apr. 22, 2021

(65) Prior Publication Data
US 2022/0369896 A1   Nov. 24, 2022

(30) Foreign Application Priority Data

Oct. 17, 2019   (JP) ................................ 2019-190065

(51) Int. Cl.
*A61B 1/018*   (2006.01)
*A61B 1/005*   (2006.01)

(52) U.S. Cl.
CPC .............. *A61B 1/018* (2013.01); *A61B 1/005* (2013.01)

(58) Field of Classification Search
CPC ... A61B 1/00078; A61B 1/0011; A61B 1/012; A61B 1/015; A61B 1/018;
(Continued)

(56) References Cited

U.S. PATENT DOCUMENTS 5,529,820 A * 6/1996 Nomi .................... B29C 67/202
428/36.5
5,789,047 A   8/1998 Sasaki et al.
(Continued)

FOREIGN PATENT DOCUMENTS

JP            7-1630 A     1/1995
JP        2001-46314 A    2/2001
(Continued)

OTHER PUBLICATIONS

Supplementary European Search Report issued in European application 20877921.5, dated Oct. 10, 2023.
(Continued)

*Primary Examiner* — Michael J Carey
*Assistant Examiner* — Stephen Floyd London
(74) *Attorney, Agent, or Firm* — GREENBLUM & BERNSTEIN, P.L.C.

(57) ABSTRACT

Provided is an endoscope capable of effectively suppressing breakage of a channel while sufficiently exhibiting performance of a plurality of portions having different degrees of bending. The endoscope includes an insertion portion and a channel arranged inside the insertion portion. The insertion portion includes a bending section that is bendable based on an operation, and a flexible tube portion that is bendable by an external force unrelated to the operation. The channel includes an inner layer and an outer layer formed outside the inner layer, the inner layer is made of polytetrafluoroethylene having a solid structure, and the outer layer is made of polytetrafluoroethylene having a porous structure. A porosity of the outer layer in the bending section is smaller than a porosity of the outer layer in the flexible tube portion.

3 Claims, 5 Drawing Sheets

(58) Field of Classification Search
CPC ...... A61M 25/0045; A61M 2025/0046; A61M 2025/0047; A61M 2025/0048; Y10T 428/1376
See application file for complete search history.

(56) References Cited

U.S. PATENT DOCUMENTS

| | | | | |
|---|---|---|---|---|
| 5,885,209 | A * | 3/1999 | Green | A61B 1/018 600/153 |
| 2010/0256445 | A1 * | 10/2010 | Fitzpatrick | A61B 1/00071 600/101 |
| 2011/0118628 | A1 * | 5/2011 | Zhou | A61M 25/09 600/585 |
| 2013/0253268 | A1 | 9/2013 | Okada et al. | |
| 2019/0246885 | A1 * | 8/2019 | Karikomi | A61B 1/015 |
| 2020/0206458 | A1 * | 7/2020 | Mullins | A61M 1/84 |
| 2021/0219827 | A1 * | 7/2021 | Ueda | A61B 1/005 |
| 2021/0290045 | A1 * | 9/2021 | Takeuchi | A61B 1/0014 |
| 2022/0022731 | A1 * | 1/2022 | Takao | G02B 23/24 |

FOREIGN PATENT DOCUMENTS

| | | |
|---|---|---|
| JP | 2012-153076 A | 8/2012 |
| JP | 2015-175385 A | 10/2015 |
| WO | 2008/088087 A2 | 7/2008 |
| WO | 2012/077760 A1 | 6/2012 |

OTHER PUBLICATIONS

International Search Report (ISR) dated Nov. 2, 2020 filed in PCT/JP2020/037103.
First Office Action issued in Chinese application No. 202080072454.3, dated Mar. 14, 2025, together with an English translation.

* cited by examiner

ENDOSCOPE

TECHNICAL FIELD

The present invention relates to an endoscope.

BACKGROUND ART

An endoscope device generally includes an insertion portion to be inserted into a body (such as a digestive organ) of a subject. The insertion portion includes a light guide configured for transmission of light and an electrical wiring for transmission of an electrical signal from an imaging unit. In addition, the insertion portion includes a channel configured for water supply or air supply, and a treatment instrument channel configured for insertion and removal a treatment instrument therein.

The insertion portion of the endoscope is required to flexibly change its shape in the body of the subject. For this reason, it is desirable that various channels included inside the insertion portion also have high pliability.

However, if the pliability of a channel increases, the possibility that buckling occurs in the channel increases. Further, in the case of the treatment instrument channel, an inner wall may be scraped by insertion and removal of the treatment instrument so that the channel may be broken. For this reason, for example, in endoscopes disclosed in Patent Literatures 1 and 2, a treatment instrument channel has a two-layer structure in which an inner layer is made of polytetrafluoroethylene (PTFE) having a solid structure and an outer layer is made of PTFE having a porous structure.

Meanwhile, the insertion portion of the endoscope generally includes a bending section, which can be actively bent by an operation of an operator, at a distal end. Further, the insertion portion also includes a flexible tube portion that is passively bent regardless of the operation of the operator, for example, when a distal end portion abuts on a wall surface of a digestive organ. In this manner, the insertion portion has the bending section capable of the active bending operation and the flexible tube portion in which only the passive bending operation occurs, and thus, it is easy to capture an image of an arbitrary point inside the digestive organ. Note that the flexible tube portion is sometimes further divided into a plurality of portions having different degrees of bending.

In this manner, the conventional endoscope includes the bending section capable of the active bending operation and the flexible tube portion in which the passive bending operation occurs. In the conventional endoscope, however, the degree of pliability of the treatment instrument channel is substantially uniform over the entire length of the bending section and the insertion portion. For this reason, there may be a case where it is difficult to obtain an expected operation without sufficiently obtaining the degree of pliability of the flexible tube portion. Conversely, if the degree of pliability of the channel in the bending section is high, the breakage of the channel including buckling of the channel or the like sometimes occurs.

CITATION LIST

Patent Literature

Patent Literature 1: JP 2001-46314 A
Patent Literature 2: WO 2008/088087 A

SUMMARY OF INVENTION

Technical Problem

An object of the present invention is to provide an endoscope capable of effectively suppressing breakage of a channel while sufficiently exhibiting performance of a plurality of portions having different degrees of bending.

Solution to Problem

In order to solve the above problems, an endoscope according to the present invention includes an insertion portion and a channel arranged inside the insertion portion. The insertion portion includes a bending section that is bendable based on an operation, and a flexible tube portion that is bendable by an external force unrelated to the operation. The channel includes an inner layer and an outer layer formed outside the inner layer, the inner layer is made of polytetrafluoroethylene having a solid structure, and the outer layer is made of polytetrafluoroethylene having a porous structure. A porosity of the outer layer in the bending section is smaller than a porosity of the outer layer in the flexible tube portion.

Advantageous Effects of Invention

According to the endoscope of the present invention, it is possible to provide the endoscope capable of effectively suppressing the breakage of the channel while sufficiently exhibiting the performance of the plurality of portions having different degrees of bending.

DESCRIPTION OF EMBODIMENTS

Hereinafter, the present embodiments will be described with reference to the accompanying drawings. In the accompanying drawings, functionally identical elements may be represented by the same number. Note that the accompanying drawings illustrate embodiments and implementation examples conforming to principles of the present disclosure, but these are for understanding of the present disclosure and are not used to interpret the present disclosure in a limited manner. The description in this specification is merely exemplary and is not intended to limit the significance of the claims or applications of the present disclosure in any way.

The present embodiments have been described in sufficient detail to enable those skilled in the art to practice the present disclosure, but it should be understood that other implementations and modes may be made and that modifications in configurations and structures and replacements of various elements are possible without departing from the scope and spirit of the technical idea of the present disclosure. Therefore, the following description should not be interpreted as being limited thereto.

First Embodiment

Figure 1:
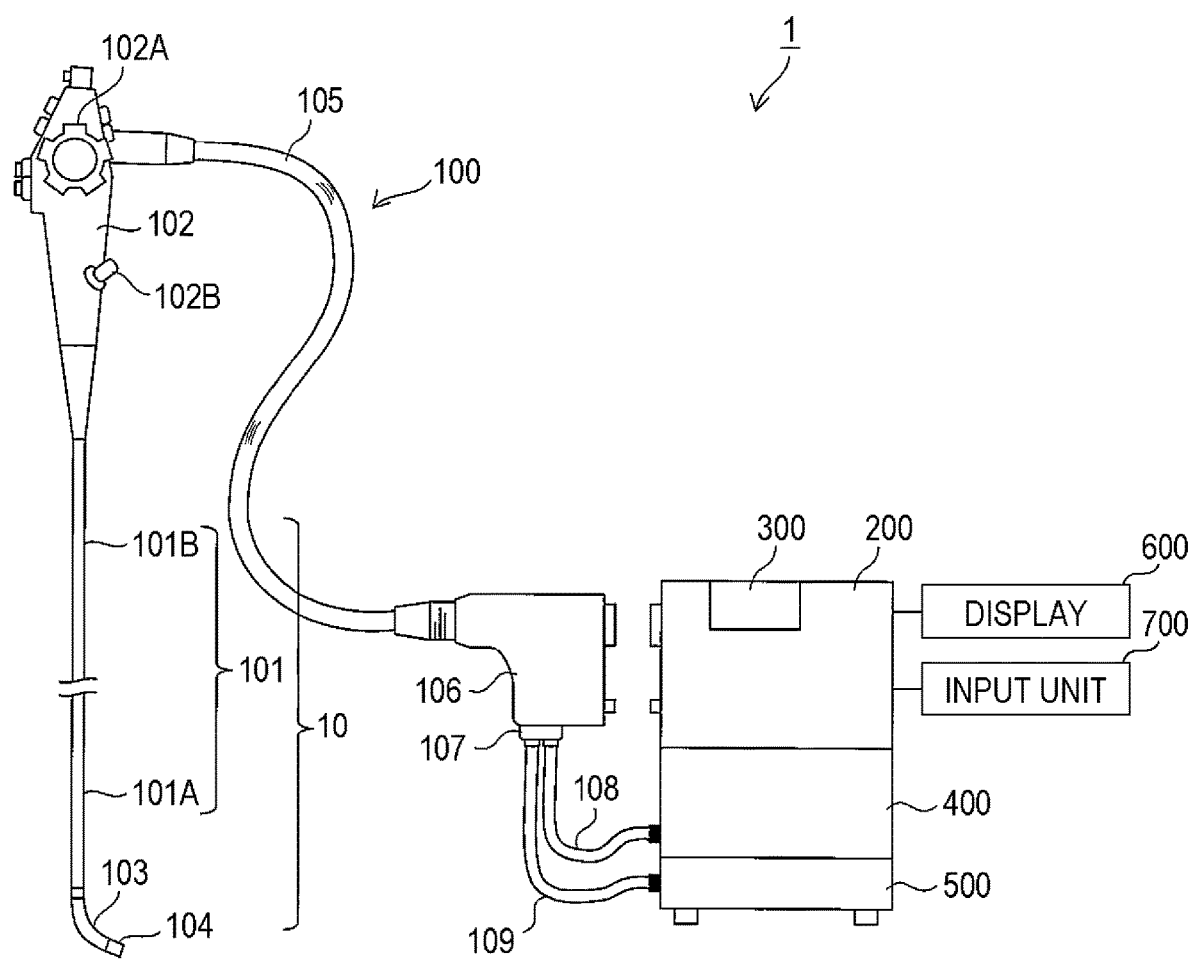
FIG. 1 is an exterior view of an endoscope system 1 according to a first embodiment of the present invention.
Figure 2:
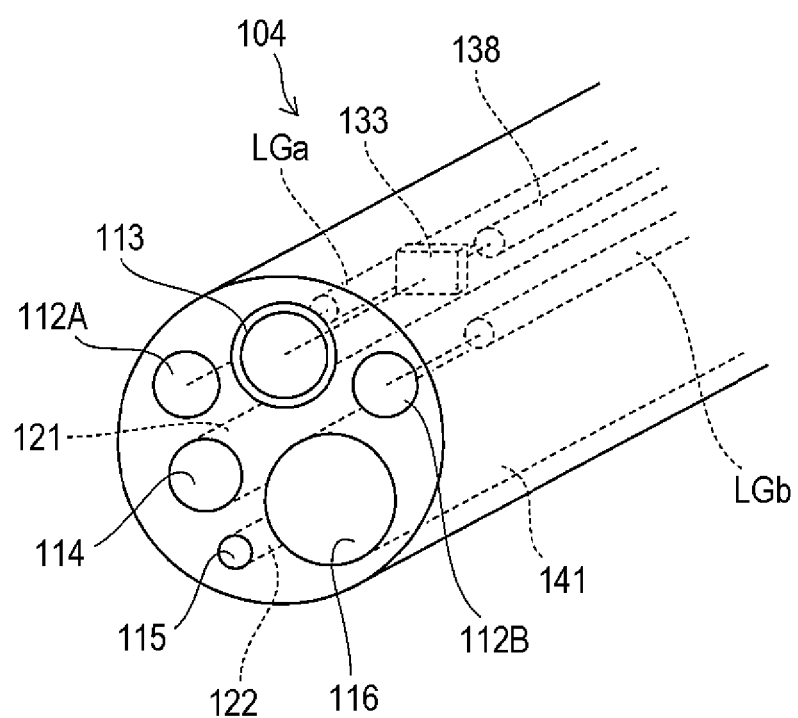
FIG. 2 is a schematic perspective view illustrating a structure of a portion of a distal end portion 104 of an endoscope 100.

First, an endoscope system according to an embodiment of the present invention will be described in detail. FIG. 1 is an exterior view of an endoscope system 1 according to the first embodiment, and FIG. 2 is a perspective view illustrating a structure of a distal end portion 104 of an endoscope 100. The endoscope system 1 generally includes the endoscope 100, a processor 200, a light source device 300, a water/air supply unit 400, a suction unit 500, a display 600, and an input unit 700.

The endoscope 100 is configured to be insertable into a body of an object and has a function of capturing an image of a subject and transmitting an image signal of the captured image to the processor 200. The processor 200 receives the image signal from the endoscope 100 and performs predetermined signal processing.

The light source device 300 is configured to be connectable to the processor 200, and includes a light source that emits irradiation light configured for irradiation of the object therein. The light from the light source is emitted toward the subject through a light guide to be described later. The light source device 300 may be configured separately from the processor 200 and connectable to the processor 200, or may be incorporated in the processor 200.

The water/air supply unit 400 includes an air pump configured to discharge a water flow or an air flow supplied to the subject. The suction unit 500 includes a pump and a tank (not illustrated) configured to suck a body fluid and an excised material sucked from the body of the subject through the endoscope 100.

The display 600 is a display device configured to perform display based on, for example, a data processing result in the processor 200. Further, the input unit 700 is a device configured to input instructions from an operator in various measurement operations.

The endoscope 100 includes an insertion portion 10, a hand operation unit 102, a universal cable 105, and a connector unit 106. The insertion portion 10 further includes a flexible tube portion 101, a connecting portion 103A, a bending section 103, and a distal end portion 104.

As illustrated in FIG. 1, the insertion portion 10 of the endoscope 100 includes the flexible tube portion 101 which has flexibility and is configured to be inserted into the body of the subject. The flexible tube portion 101 is connected to the hand operation unit 102 at one end thereof. The hand operation unit 102 includes, for example, a bending operation knob 102A and other operation units that can be operated by a user, and is a portion configured to allow the operator to perform various operations for imaging by the endoscope system 1. Note that the hand operation unit 102 is provided with a treatment instrument insertion port 102B for insertion of a treatment instrument.

In the flexible tube portion 101, a portion close to the bending section 103 is a first flexible tube portion 101A, and a portion close to the hand operation unit 102 is a second flexible tube portion 101B. A shape of the bending section 103 can be actively changed by the operation of the bending operation knob 102A by the operator, but the first flexible tube portion 101A is a portion whose shape is passively changed due to an external force unrelated to the operation of the bending operation knob 102A, for example, an external force caused by the distal end portion 104 or the bending section 103 abutting on a wall surface of a digestive organ. The same also applies to the second flexible tube portion 101B, but the degree of change in shape is smaller (the maximum curvature radius is larger) than that of the first flexible tube portion 101A. Note that the flexible tube portion 101 has two types of flexible tube portions in the example of FIG. 1, but the present invention is not limited thereto, and three or more types of flexible tube portions may be provided, or one type may be provided.

The bending section 103 (active bending section) configured to be bendable is provided at a distal end of the flexible tube portion 101. As described above, the bending section 103 is bent by pulling an operation wire (not illustrated in FIG. 1) in conjunction with a rotation operation of the bending operation knob 102A provided in the hand operation unit 102. Note that the connecting portion 103A that is not deformed by a bending wire W or the external force may be provided between the bending section 103 and the first flexible tube portion 101A.

Furthermore, the distal end portion 104 including an image sensor (imaging unit) is connected to a distal end of the bending section 103. As a direction of the distal end portion 104 changes according to a bending operation of the bending section 103 caused by the rotation operation of the bending operation knob 102A, it is possible to change an imaging area of the endoscope 100.

The universal cable 105 extends from the opposite side of the hand operation unit 102 to the connector unit 106. The universal cable 105 includes a light guide, various wirings, and various channels therein, which is similar to the insertion portion 10.

The connector unit 106 includes various connectors configured to connect the endoscope 100 to the processor 200. Further, the connector unit 106 includes a water/air supply channel 108 as a path configured to send a water flow and an air flow toward the insertion portion 10.

A structure of the distal end portion 104 of the endoscope 100 will be described with reference to FIG. 2. Light distribution lenses 112A and 112B are arranged at the distal end portion 104 of the endoscope 100, and light guides LGa and LGb extend from the distal end portion 104 to the connector unit 106 inside the insertion portion 10. Light from the light source of the light source device 300 is guided by the light guides LGa and LGb, and is emitted toward the subject by the light distribution lenses 112A and 112B arranged at the distal end portion 104.

Further, as illustrated in FIG. 2, the endoscope 100 includes an objective lens 113 and an image sensor 133 at the distal end portion 104. The objective lens 113 provided at the distal end portion 104 collects scattered light or reflected light from the subject to form an image of the subject on a light receiving surface of the image sensor 133.

As an example, the image sensor 133 can be configured using a charge coupled device (CCD) or a complementary metal oxide semiconductor sensor (CMOS sensor). The image sensor 133 is controlled by signals (a gain control signal, an exposure control signal, a shutter speed control signal, and the like) supplied from the processor 200 through an electrical wiring 138, and supplies an image signal of a captured image to the processor 200 through the electrical wiring 138 and an A/D conversion circuit (not illustrated).

Further, an air/water supply port 114, an auxiliary water supply port 115, and a treatment instrument port 116 are provided, as end portions or openings of various channels, on an end surface of the distal end portion 104. The air/water supply port 114 (nozzle) is connected to an air/water supply channel 121 to introduce a water flow or an air flow for cleaning or the like of the distal end portion 104.

Further, the auxiliary water supply port 115 is connected to an auxiliary water supply channel 122 to introduce the auxiliary water supply for removing dirt in the visual field. The channels 121 to 122 are arranged so as to extend along the inside of the distal end portion 104, the bending section 103, the insertion portion 10, the hand operation unit 102, and the universal cable 105.

In addition to the channels 121 to 122, a treatment instrument channel 141 is provided inside the endoscope 100. A treatment instrument such as forceps is arranged inside the treatment instrument channel 141 so as to freely advance and retreat. A distal end of the treatment instrument channel 141 forms the treatment instrument port 116 at the distal end portion 104. Note that the treatment instrument channel 141 may also serve as a suction channel.

Figure 3:
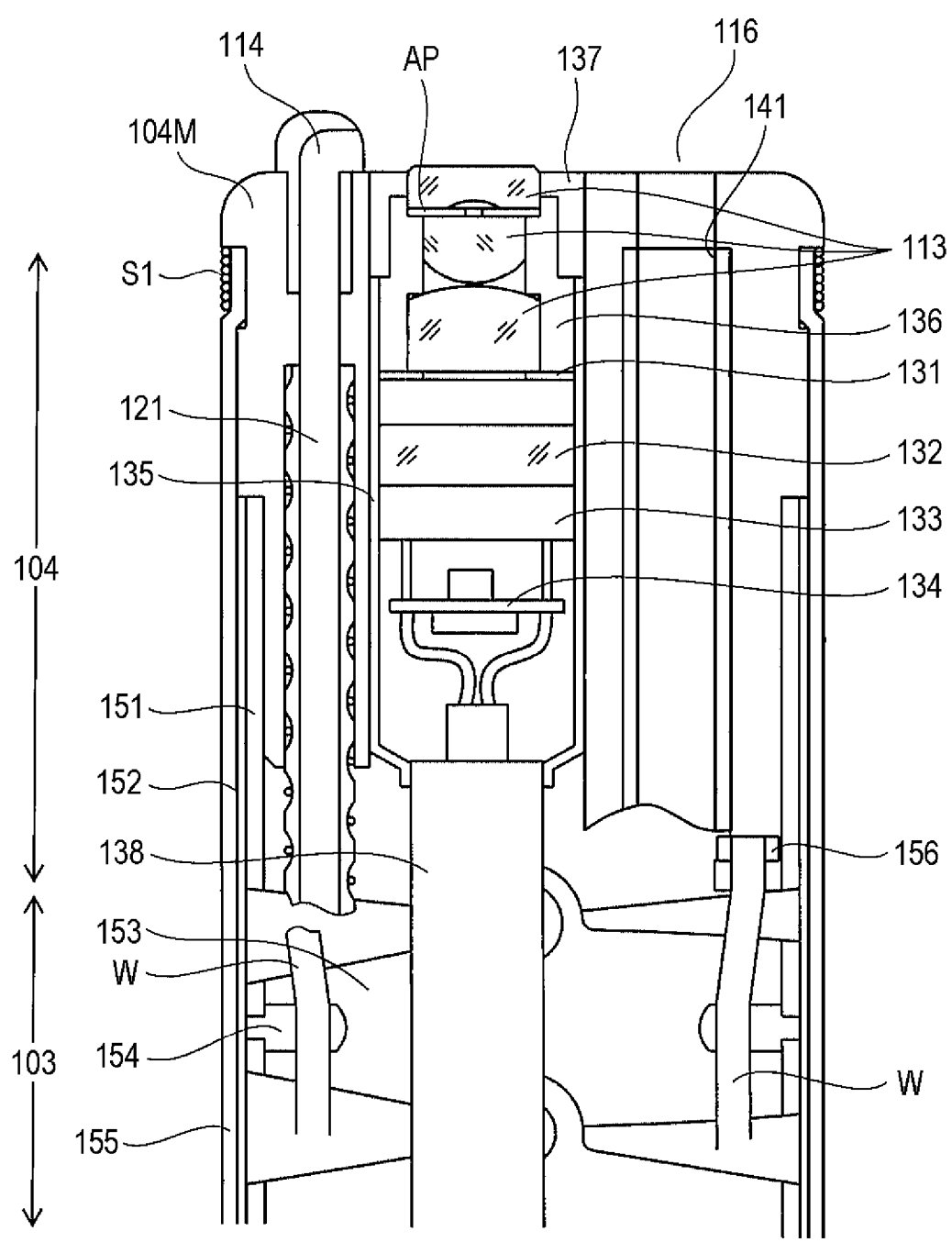
FIG. 3 is a cross-sectional view illustrating a cross-sectional structure of the distal end portion 104 in detail.

A cross-sectional structure of the distal end portion 104 will be described in more detail with reference to FIG. 3. This cross-sectional view illustrates details of structures of the objective lens 113 to the electrical wiring 138, the air/water supply channel 121, and the treatment instrument channel 141. Structures of the light distribution lenses 112A and 112B and the light guides LGa and LGb are not illustrated. Further, a structure of the auxiliary water supply channel 122 is not illustrated either.

The distal end portion 104 has a distal-end rigid portion 104M. The distal-end rigid portion 104M includes holes respectively forming the air/water supply port 114, the auxiliary water supply port 115, and the treatment instrument port 116 described above. As illustrated in FIG. 3, the air/water supply channel 121 and the treatment instrument channel 141 are inserted into corresponding holes of the distal-end rigid portion 104M.

The distal-end rigid portion 104M also has a hole configured for fitting of a lens frame 136 that holds the objective lens 113, an aperture AP, and a light shielding mask 131. The lens frame 136 is fixed to the hole of the distal-end rigid portion 104M with a sealant 137 interposed therebetween.

Meanwhile, as an example, the light shielding mask 131, a cover glass 132, the image sensor (CCD) 133, and a circuit board 134 are held by a CCD unit frame 135 on the rear side of the objective lens 113, and the CCD unit frame 135 is inserted and fixed to the hole of the distal-end rigid portion 104M. The electrical wiring 138 is connected to the circuit board 134.

The distal end portion 104 (distal-end rigid portion 104M) configured as described above is fitted into the distal end of the bending section 103. The bending section 103 is formed by rotatably connecting bending pieces 153 each of which is formed in a substantially cylindrical shape to each other by a rivet. An outer surface of the bending piece 153 is covered with a reticular tube 152. The reticular tube 152 is joined to the distal-end rigid portion 104M at its end portion through an annular joining tube 151. Further, an outer surface of the reticular tube 152 is covered with an outer rubber tube 155 made of a synthetic resin. The outer rubber tube 155 and the distal-end rigid portion 104M are fixed at end portions thereof by, for example, a fixing yarn S1.

A wire guide 154 is provided between the plurality of bending pieces 153, and the bending wire W for the bending operation passes through the wire guide 154. For example, four bending wires W are provided at substantially equal intervals in the circumferential direction in one insertion portion 10. One end of each of the bending wires W is fixed to the foremost bending piece 153. The other end of the bending wire W is tensioned and relaxed by the operation of the bending operation knob 102A, whereby the bending section 103 is bent.

Figure 4:
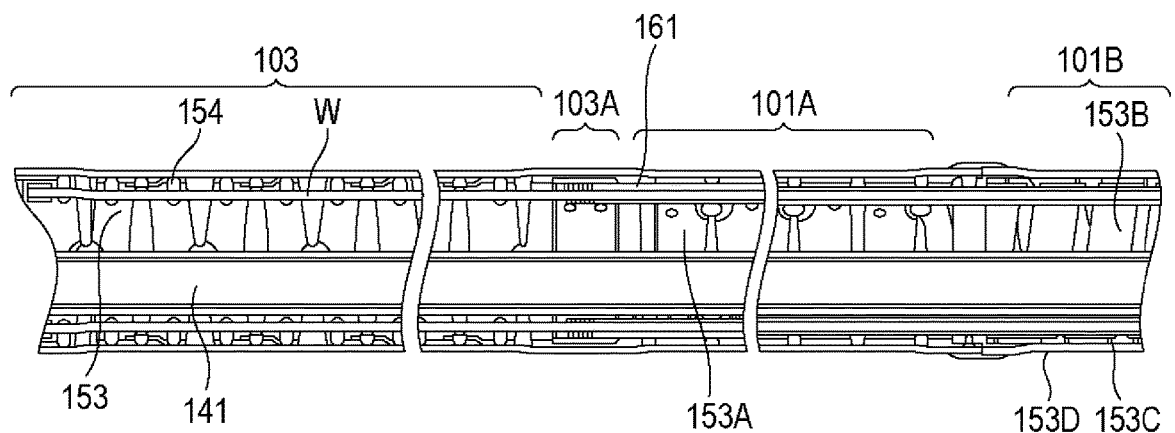
FIG. 4 is a cross-sectional view illustrating structures of a connecting portion 103A, a first flexible tube portion 101A, and a second flexible tube portion 101B.

Next, structures of the connecting portion 103A, the first flexible tube portion 101A, and the second flexible tube portion 101B will be described with reference to FIG. 4.

As described above, the connecting portion 103A is a member that connects the bending section 103 and the first flexible tube portion 101A, and is a rigid portion whose outer shape is not deformed by the operation of the bending wire W or the external force. The first flexible tube portion 101A includes a plurality of bending pieces 153A, which is similar to the bending section 103. The bending pieces 153A are rotatably connected to each other by a rivet, which is similar to the bending pieces 153 Further, as an example, the second flexible tube portion 101B may include a spiral tube 153B (flat coil made of metal), a metal mesh 153C, and an outer resin 153D (polyurethane or the like) from the inside.

Further, the first flexible tube portion 101A and the second flexible tube portion 101B are provided with a coil sheath 161 configured to allow the bending wire W extending from the hand operation unit 102 to pass therethrough. The bending wire W is arranged so as to be slidable inside the coil sheath 161, and thus, the shapes of the first flexible tube portion 101A and the second flexible tube portion 101B do not change even when the bending wire W is tensioned or relaxed. The first flexible tube portion 101A and the second flexible tube portion 101B can be deformed within a movable range of the bending piece 153A and the spiral tube 153B by the external force or the like caused by, for example, the outer wall of the digestive organ abutting on the insertion portion 10.

As described above, the bending section 103, the first flexible tube portion 101A, and the second flexible tube portion 101B can be deformed by the operation of the bending wire W or the external force, but the deformation limits (maximum curvature radii) are different from each other. Further, since the maximum curvature radii are different, buckling strengths (kink resistances) required for tubes for channels inserted therein are also different from each other.

Figure 5:
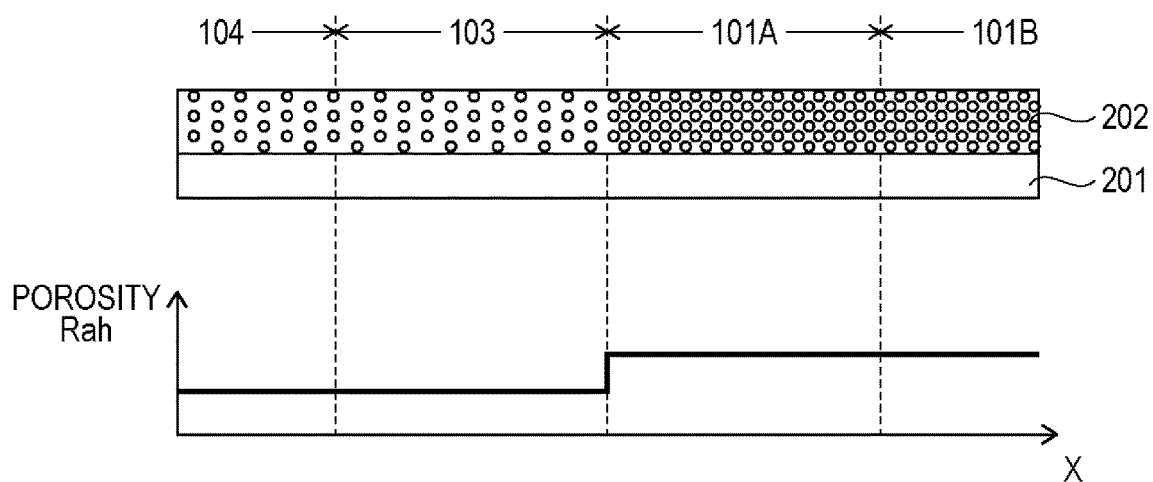
FIG. 5 is a schematic view illustrating a structure of a treatment instrument channel 141 according to the first embodiment.

In the first embodiment, the treatment instrument channel 141 is configured as illustrated in FIG. 5 such that characteristics of the bending section 103, the first flexible tube portion 101A, and the second flexible tube portion 101B can be maximized. FIG. 5 is a cross-sectional view illustrating a cross-sectional structure of the treatment instrument channel 141 and a graph illustrating a characteristic (porosity Rah) thereof.

The treatment instrument channel 141 has a two-layer structure of an inner layer 201 and an outer layer 202 arranged outside the inner layer 201. The inner layer 201 is made of PTFE having a solid structure over the entire length (the distal end portion 104 to the second flexible tube portion 101B) in order to suppress breakage due to contact with the treatment instrument passing through the channel. On the other hand, the outer layer 202 is made of porous PTFE. The PTFE having the solid structure is hard and has a high resistance to breakage, but is easily buckled, whereas the porous PTFE is flexible and has a low resistance to breakage, but is hardly buckled. Since the treatment instrument channel 141 has the two-layer structure of the PTFE having the solid structure and the porous PTFE, both the resistance to breakage and buckling resistance can be achieved. In other words, the PTFE having the solid structure of the inner layer 201 is held by the porous PTFE of the outer layer 202 that is hardly buckled, so that a tube that is flexible but hardly buckled can be obtained.

In addition, the porous PTFE of the outer layer 202 of the first embodiment has a different porosity Rah depending on a location. When the porosity Rah of the outer layer 202 is large, the pliability of the treatment instrument channel 141 is enhanced accordingly.

The outer layer 202 located in the bending section 103 that is bendable by the bending operation knob 102A has q porosity Rah set to about 10 to 40%, for example. On the other hand, the outer layer 202 located in the first flexible tube portion 101A and the second flexible tube portion 101B has a higher porosity Rah (for example, 30 to 80% which is a value higher than that of the inside of the bending section 103) than the inside of the bending section 103.

Since the degree of bending of the bending section 103 can be adjusted by operating the bending wire W with the bending operation knob 102A, the bending section 103 does not need to have a higher pliability than that of the insertion portion 10. Therefore, it is sufficient for the outer layer 202 in the bending section 103 to have pliability to such an extent that the operation of the bending wire W is not hindered.

On the other hand, a curvature change larger than that of the insertion portion 10 is given to the bending section 103 by the bending wire W, and thus, it is required to suppress the breakage of the channel due to buckling. For this reason, the outer layer 202 of the treatment instrument channel 141 inside the bending section 103 is provided with a smaller porosity than those of the first flexible tube portion 101A and the second flexible tube portion 101B. As a result, the bending section 103 has pliability to such an extent that the bending wire W can be deformed, and has a high resistance to the buckling.

On the other hand, the first flexible tube portion 101A and the second flexible tube portion 101B need to be flexibly deformed by the external force based on abutment of the distal end portion 104 or the like on the inner wall of the digestive organ or the like, and to have a higher pliability than that of the bending section 103 in order reduce burden on a patient. The outer layer 202 of the treatment instrument channel 141 of the first embodiment is provided with a higher porosity Rah inside the first flexible tube portion 101A and the second flexible tube portion 101B than inside the bending section 103. As a result, the first flexible tube portion 101A and the second flexible tube portion 101B are provided with a high pliability, and the burden on the patient is reduced. Note that the porosities Rah of the first flexible tube portion 101A and the second flexible tube portion 101B are the same in the above example, but different porosities may be given.

Note that the porosity Rah of the outer layer 202 inside the distal end portion 104 is arbitrary, and may be, for example, the same as the porosity Rah inside the bending section 103. Since the distal end portion 104 is not bent (deformed), the hardness of the treatment instrument channel 141 passing through the distal end portion is irrelevant. Only the outer layer 202 of the distal end portion 104 may be made of the PTFE having the solid structure.

As described above, in the endoscope of the first embodiment, the treatment instrument channel 141 has the two-layer structure of the inner layer 201 and the outer layer 202, the inner layer 201 is made of polytetrafluoroethylene having a solid structure, the outer layer 202 is made of polytetrafluoroethylene having a porous structure, and the porosity of the outer layer 202 in the bending section 103 is smaller than the porosity of the outer layer 202 in the first flexible tube portion 101A and the second flexible tube portion 101B. As a result, a certain degree of pliability and a sufficient buckling resistance can be obtained in the bending section 103, while a high pliability can be obtained in the first flexible tube portion 101A and the second flexible tube portion 101B. Therefore, it is possible to provide the endoscope that sufficiently exhibits the functions of the flexible tube portion 101 and the bending section 103. Note that the two-layer structure is adopted for the treatment instrument channel 141 in the above-described example, but it goes without saying that a similar structure may be adopted for a channel other than the treatment instrument channel 141.

[Second Embodiment]

Figure 6:
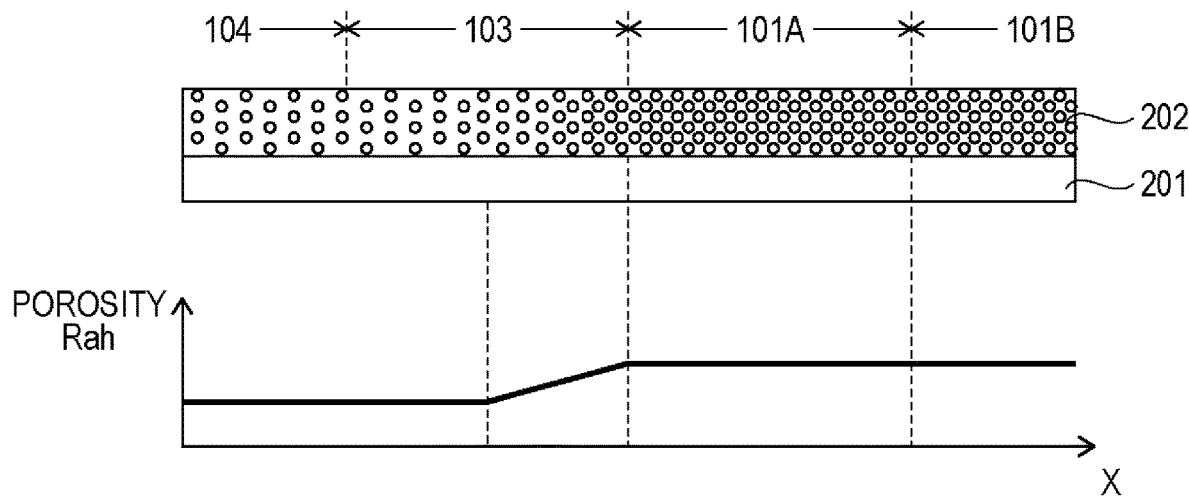
FIG. 6 is a schematic view illustrating a structure of a treatment instrument channel 141 according to a second embodiment.

Next, an endoscope according to a second embodiment will be described with reference to FIG. 6. The overall configuration of the endoscope of the second embodiment is similar to that of the first embodiment (FIG. 1). Further, configurations of the distal end portion 104, the bending section 103, and the insertion portion 10 are also similar to those of the first embodiment (FIGS. 2 to 3) except for the following points.

Figure 7:
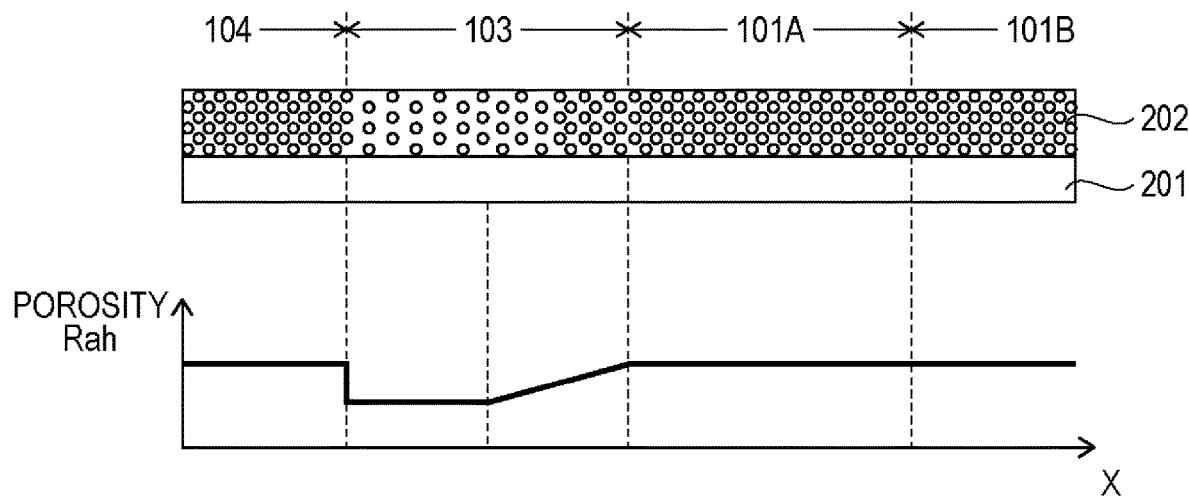
FIG. 7 is a schematic view illustrating a structure of a treatment instrument channel 141 according to a modification of the second embodiment.

The second embodiment is similar to the first embodiment in that the porosity Rah of the outer layer 202 inside the bending section 103 is smaller than the porosity Rah of the outer layer 202 inside the flexible tube portion 101. However, the porosity Rah of the bending section 103 is set to a low value on the distal end portion 104 side, gradually increases at an end portion of the bending section 103 on the first flexible tube portion 101A side, and becomes substantially the same as the porosity Rah inside the first flexible tube portion 101A in the vicinity of a boundary between the bending section 103 and the flexible tube portion 101. Note that the porosity Rah of the outer layer 202 inside the distal end portion 104 may be substantially the same as the porosity Rah inside the bending section 103 as in the first embodiment, but may be a value larger than the porosity Rah inside the bending section 103 as illustrated in FIG. 7. Note that the boundary between the bending section 103 and the flexible tube portion 101 does not need to be strictly defined, and can be set at any location in the connecting portion 0103A.

According to the configuration of the second embodiment, the function of the bending section 103 can be further enhanced. In the bending section 103, typically, a curvature is small at the end portion on the distal end portion 104 side, and the curvature is large on the flexible tube portion 101 side. For this reason, when the distribution of the porosity Rah as illustrated in FIG. 6 is adopted inside the bending section 103, a buckling resistance can be enhanced at the end portion of the bending section 103 on the distal end portion 104 side, and pliability can be enhanced on the insertion portion 10 side.

[Others]

The present invention is not limited to the above-described embodiments, and includes various modifications. For example, the above-described embodiments have been described in detail in order to describe the present invention in an easy-to-understand manner, and are not necessarily limited to those having all the described configurations. Further, a part of a configuration of a certain embodiment can be replaced with a configuration of another embodiment, and a configuration of another embodiment can be added to a configuration of a certain embodiment. Further, it is possible to perform addition, deletion, and replacement of configurations of other embodiments on a part of the configurations of each of the embodiments.

REFERENCE SIGNS LIST 1 endoscope system
100 endoscope
10 insertion portion
101 flexible tube portion
101A first flexible tube portion
101B second flexible tube portion 102 hand operation unit
102A bending operation knob
103 bending section
104 distal end portion
105 universal cable
106 connector unit
108 water/air supply channel
LGa, LGb light guide
112A, 112B light distribution lens
113 objective lens
114 air/water supply port
115 auxiliary water supply port
116 treatment instrument port
121 air/water supply channel
122 auxiliary water supply channel
141 treatment instrument channel
133 image sensor
134 circuit board
135 CCD unit frame
136 lens frame
137 sealant
138 electrical wiring
161 coil sheath
200 processor
300 light source device
400 water/air supply unit
500 suction unit
600 display
700 input unit

The invention claimed is:

1. An endoscope comprising:
an insertion portion; and
a channel arranged inside the insertion portion,
wherein the insertion portion includes:
a bending section that is bendable based on an operation; and
a flexible tube portion that is bendable by an external force unrelated to the operation, wherein:
the channel includes an inner layer and an outer layer formed outside the inner layer,
the inner layer is made of polytetrafluoroethylene having a solid structure,
the outer layer is made of polytetrafluoroethylene having a first porous structure including a first porosity in the bending section and further having a second porous structure including a second porosity in the flexible tube portion, and
the first porosity of the outer layer in the bending section is smaller than the second porosity of the outer layer in the flexible tube portion.

2. The endoscope according to claim 1, wherein the first porosity of the outer layer in the bending section gradually increases toward an end portion point of the flexible tube portion.

3. The endoscope according to claim 1, wherein the bending section comprises a plurality of bending pieces.

* * * * *